US006907282B2

(12) United States Patent
Siochi (10) Patent No.: US 6,907,282 B2
(45) Date of Patent: Jun. 14, 2005

(54) INTENSITY MAP RESAMPLING FOR MULTI-LEAF COLLIMATOR COMPATIBILITY

(75) Inventor: Ramon Alfredo Carvalho Siochi, Apex, NC (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 594 days.

(21) Appl. No.: 10/037,330

(22) Filed: Nov. 9, 2001

(65) Prior Publication Data

US 2003/0091146 A1 May 15, 2003

(51) Int. Cl.[7] .............................................. A61B 5/05
(52) U.S. Cl. ...................... 600/411; 600/407; 600/425; 600/427; 600/429; 600/439; 601/2; 601/3; 601/4; 128/922; 128/898; 345/9; 345/113
(58) Field of Search ................................ 600/407–436, 600/439; 601/1–5; 128/922, 898; 345/9, 113

(56) References Cited

U.S. PATENT DOCUMENTS

| | | | | |
|---|---|---|---|---|
| 5,418,827 A | * | 5/1995 | Deasy et al. ................... 378/65 |
| 5,548,627 A | * | 8/1996 | Swerdloff et al. .............. 378/4 |
| 5,647,663 A | * | 7/1997 | Holmes ....................... 600/407 |
| 5,663,999 A | | 9/1997 | Siochi .......................... 378/65 |
| 5,724,403 A | | 3/1998 | Siochi et al. ................ 378/150 |
| 5,995,864 A | * | 11/1999 | Wessol et al. ............... 600/436 |
| 6,029,079 A | * | 2/2000 | Cox et al. .................... 600/407 |
| 6,044,126 A | * | 3/2000 | Rousseau et al. ............. 378/65 |
| 6,222,544 B1 | * | 4/2001 | Tarr et al. ................... 715/839 |

\* cited by examiner

Primary Examiner—Brian L. Casler
Assistant Examiner—William C. Jung (57) ABSTRACT

A method for converting a source intensity map into a target intensity map having a geometry compatible with a desired multi-leaf collimator configuration. The source intensity map and the target intensity map each have a geometry defining sampling points of cells within the maps. The method includes defining a field on an object for radiation delivery. The field includes a plurality of cells defining the source intensity map, each of the cells having a treatment intensity level. An intermediate intensity map geometry is created such that the intermediate map contains sampling points of the source intensity map and the target intensity map. The method further includes defining treatment intensity levels for cells of the intermediate map and calculating treatment intensity levels for cells of the target intensity map based on the intensity level of the intermediate map cells.

13 Claims, 6 Drawing Sheets

INTENSITY MAP RESAMPLING FOR MULTI-LEAF COLLIMATOR COMPATIBILITY

FIELD OF THE INVENTION

The present invention relates generally to radiation delivery with an intensity modulating multi-leaf collimator, and more particularly, to a system and method for resampling an intensity map to conform with multi-leaf collimator geometry requirements.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes to segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

Different multi-leaf collimators often have different geometry requirements for intensity maps used to define the radiation treatment. This often results in treatment planning systems having to be reconfigured to support a particular type of multi-leaf collimator. This may require waiting for the next software version to be developed and distributed with a fix to support the particular multi-leaf collimator. Alternatively, rows and columns of an intensity map can be removed and data within the remaining rows and columns shifted to fit the new geometry. However, this results in a change of the spatial distribution of a two dimensional function which is no longer accurately represented. For example, very high values may be placed in regions where lower values should be used because of shifting that occurs in locations having high gradients.

Accordingly, there is therefore, a need for a system and method that converts an intensity map that is incompatible with a particular multi-leaf collimator geometry into an intensity map that is compatible with the multi-leaf collimator geometry.

SUMMARY OF THE INVENTION

A method for converting a source intensity map into a target intensity map having a geometry compatible with a desired multi-leaf collimator configuration is disclosed. The source intensity map and the target intensity map each have a geometry defining sampling points of cells within the maps. The method includes defining a field on an object for radiation delivery. The field includes a plurality of cells defining the source intensity map, each of the cells having a treatment intensity level. An intermediate intensity map geometry is created such that the intermediate map contains sampling points of the source intensity map and the target intensity map. The method further includes defining treatment intensity levels for cells of the intermediate map and calculating treatment intensity levels for cells of the target intensity map based on the intensity level of the intermediate map cells.

A system for converting a source intensity map into a target intensity map generally comprises a processor operable to receive a source intensity map geometry, target intensity map geometry, and treatment intensity levels for cells of the source intensity map, create an intermediate map geometry containing sampling points of the source map and the target map, define treatment intensity levels for cells of the intermediate map, calculate treatment intensity levels for cells of the target intensity map based on the intensity level of the intermediate map cells, and output the target intensity map. The system further includes memory configured to at least temporarily store the source intensity map, intermediate intensity map, and the target intensity map.

The above is a brief description of some deficiencies in the prior art and advantages of the present invention. Other

BRIEF DESCRIPTION OF THE DRAWINGS

FIG. 5b is a row of an intermediate intensity map used to create a row of the target intensity map of FIG. 5c from the source intensity map of FIG. 5a.

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
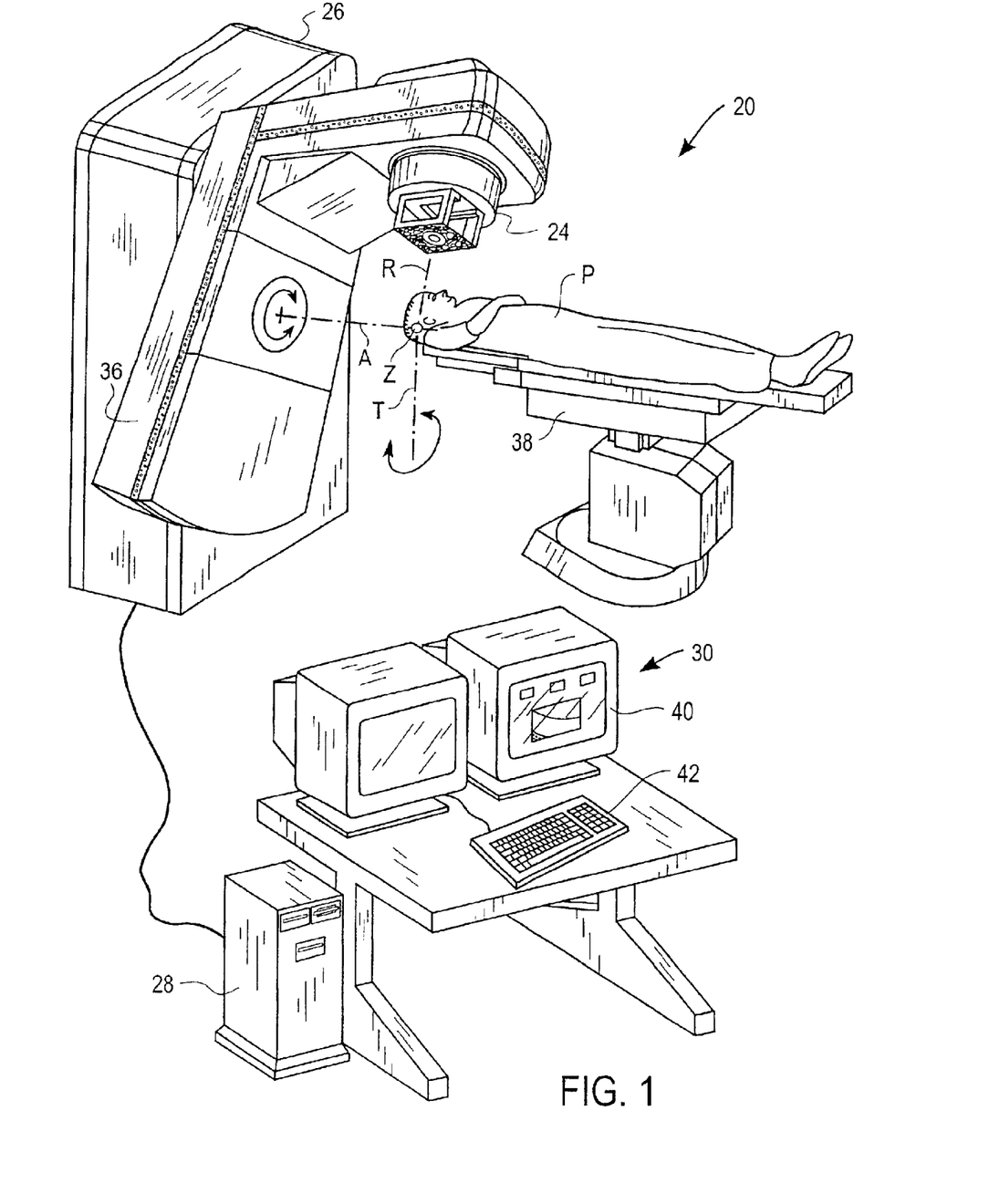
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
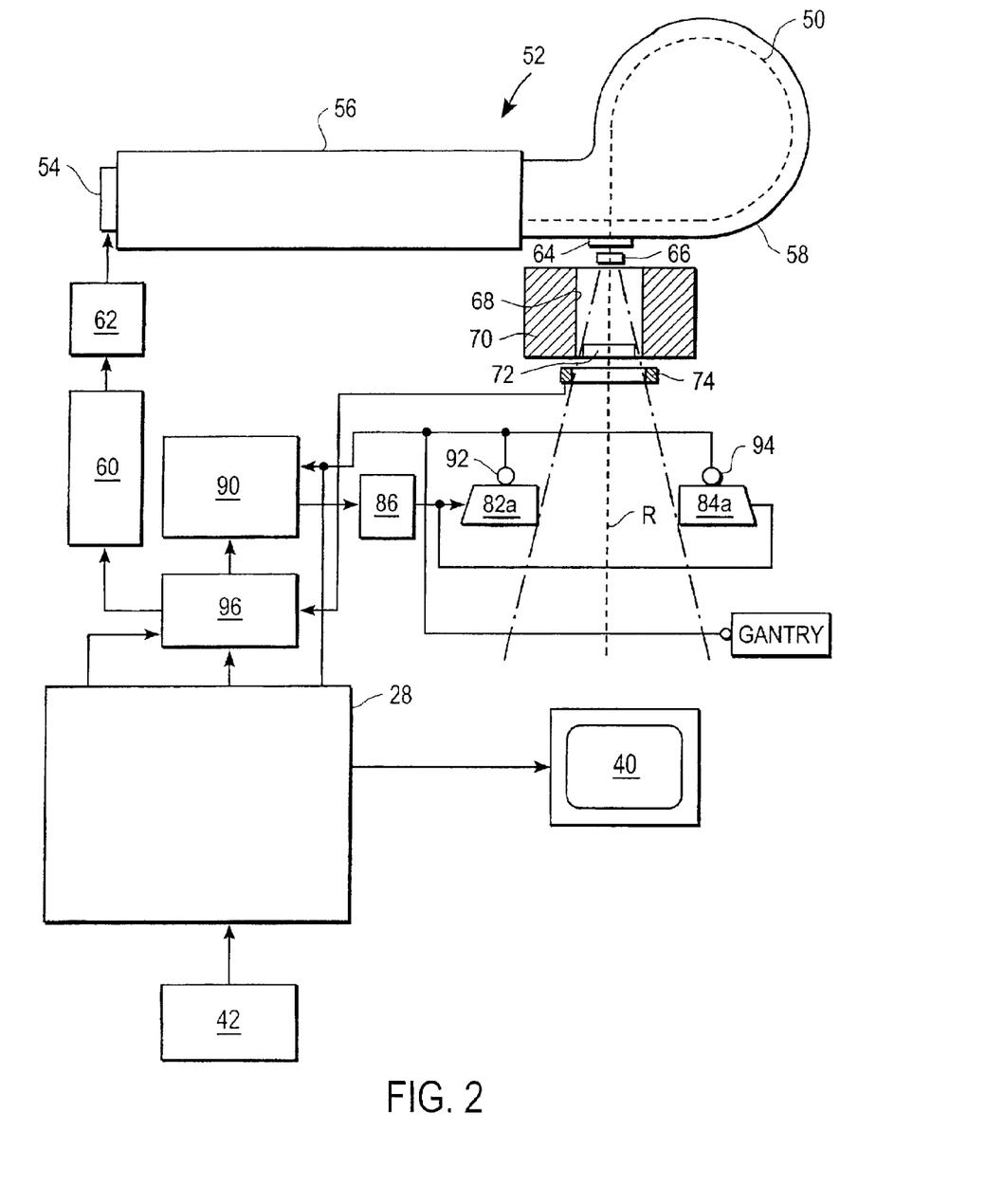
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
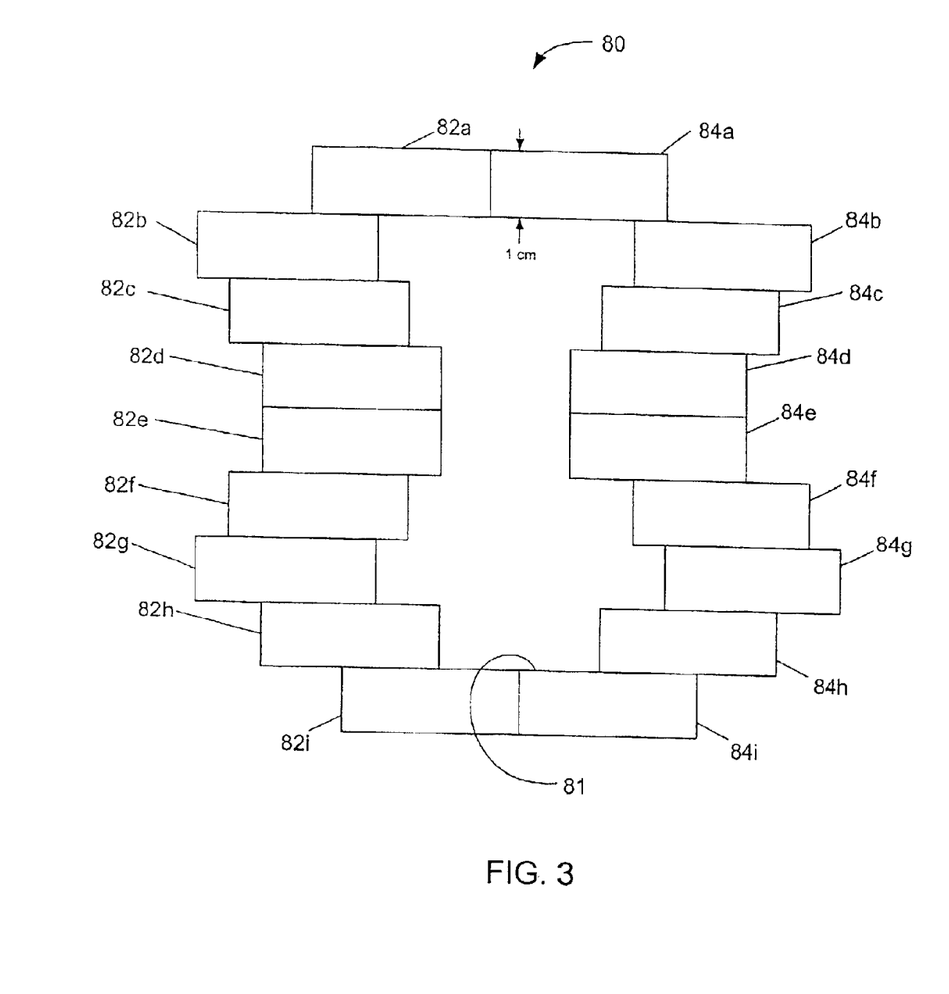
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the intensity map resampling process described below.

The intensity map is used in intensity modulation radiation therapy to describe the modulation pattern that should be delivered to the patient. The intensity map is decomposed into multi-leaf collimator shapes, therefore, it must have a geometry that is compatible with the multi-leaf collimator. In some cases an input intensity map may have the wrong geometry. For example, the map may be shifted relative to the multi-leaf collimator geometry in the case where the isocenter is inside the middle of a leaf pair, while the map may have the isocenter in between two rows instead of inside a row.

Figure 4:
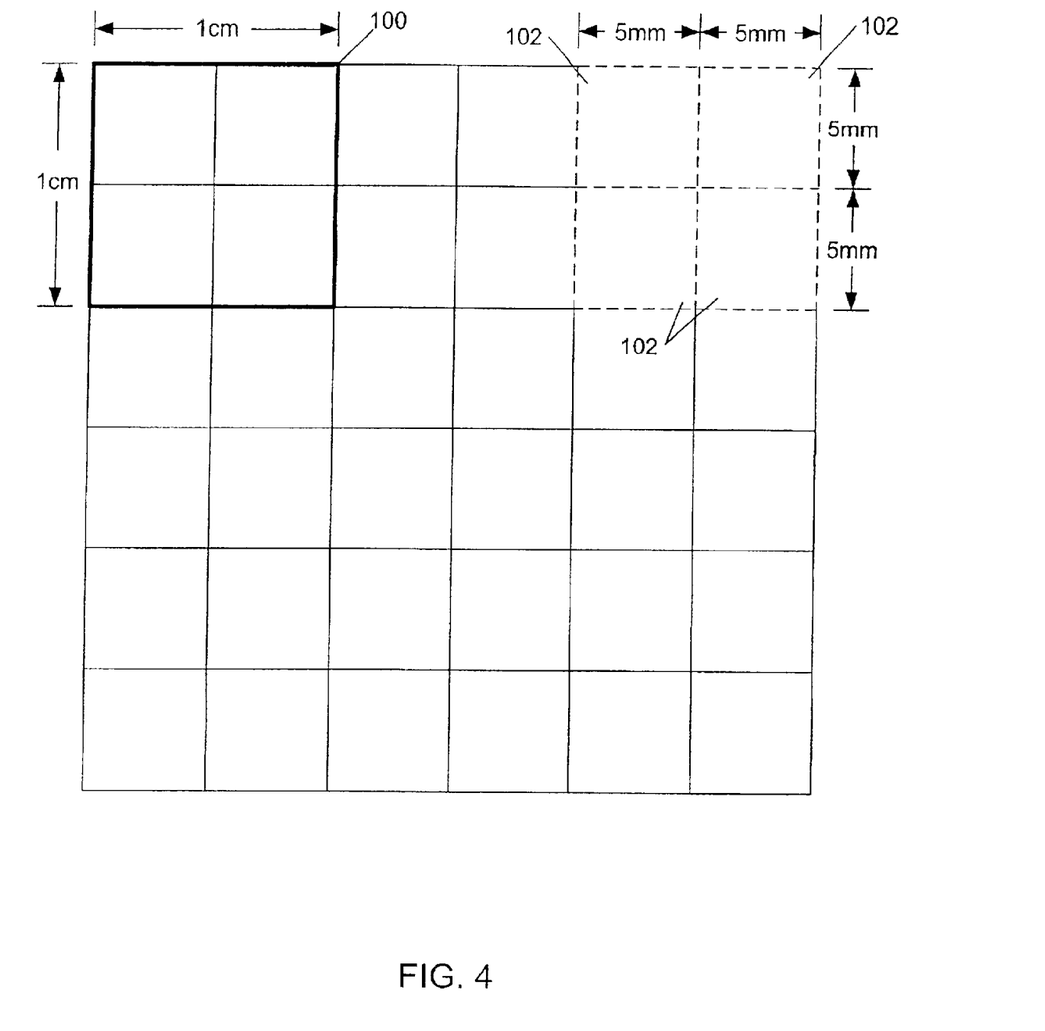
FIG. 4 is a schematic illustrating cells located in an intensity map.

Another example in which the cells of an intensity map need to be shifted is in the case of virtual micro intensity modulation radiation therapy. This process provides for the delivery of two 1 cm×0.5 cm intensity maps that are orthogonal to one another so that an effective intensity map grid size is 5 mm×5 mm. (See, U.S. Pat. No. 6,134,296, which is incorporated herein by reference in its entirety.) FIG. 4 illustrates an intensity map having a plurality of 1 cm×1 cm macrocells 100 (indicated by dark lines) divided into four 5 mm×5 mm microcells 102 (indicated by dashed lines). The 5 mm×5 mm microcells 102 are used to convert macrocell 100 into two orthogonal intensity maps (component maps), one with a resolution of 5 mm×10 mm, and the other with a resolution of 10 mm×5 mm. An example of a process for dividing the intensity map into groups of four 5 mm×5 mm microcells 102 is described in U.S. Pat. No. 6,134,296. This grouping of 5 mm×5 mm microcells 102 allows for treatment of a field with a 5 mm×5 mm resolution using a multi-leaf collimator having one centimeter leaves, as shown in FIG. 3.

For virtual micro intensity modulation radiation therapy, the 5 mm×5 mm microcells must be contained within the 1 cm×1 cm macrocells formed by the intersection of leaf pairs from orthogonal directions. If the input map has 5 mm×5 mm microcells that are centered on the isocenter, then it is shifted by 2.5 mm in the x and y directions with respect to what is required for virtual micro intensity modulation radiation therapy. The following example describes a method for resampling the intensity map so that it is compatible with the geometry of a multi-leaf collimator for virtual micro intensity modulation radiation therapy. It is to be understood, however, that the method and system of the present invention may be used to resample intensity maps for uses other than virtual micro intensity radiation therapy, without departing from the scope of the invention.

In this example, the source (or input) intensity map is configured such that the isocenter is located between two rows and the target (or output) intensity map is configured such that a row contains the isocenter. An intermediate map is created that has a configuration that is common to both the source map and the target map (i.e., contains sampling points of both the source map and the target map). The source intensity map has sampling points at the center of each of the shifted microcells at x=5n mm (where n=0, ±1, ±2, . . . ) and y=5n mm (where n=0, ±1, ±2, . . . ). The sampling points required so that virtual micro intensity modulation radiation therapy can be used are: x=2.5+5n mm (where n=0, ±1, ±2, . . . ) and y=2.5+5n mm (where n=0, ±1, ±2, . . . ). The intermediate map used to perform the conversion therefore has sampling points at x=2.5n mm (where n=0, ±1, ±2, . . . ) and y=2.5n mm (where n=0, ±1, ±2, . . . ). This intermediate intensity map contains all of the sampling points of the source map and the target map.

After determining the required sampling resolution for the intermediate map, the map needs to be filled in with the appropriate intensity values. Two methods may be used to determine the intensity values. If the source intensity map provided by the treatment planning system was downsampled from a higher resolution raw map of the treatment planning system, then the treatment planning system can be reconfigured to provide the higher resolution map as the source map. In this case the source map and the intermediate map are the same (i.e., have same geometry and intensity levels). Alternatively, the values from the source map may be extrapolated and interpolated to calculate intensity level values for the intermediate intensity map. Once the intermediate map is formed, the values are downsampled to obtain the target map, which is compatible with the geometry of the multi-leaf collimator. The only points taken from the intermediate map are those required for the target map.

Figure 5A:
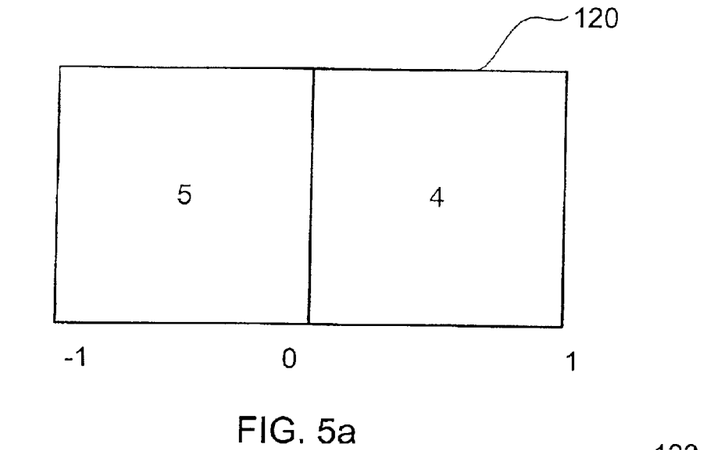
FIG. 5a is a row of a source intensity map.
Figure 5B:
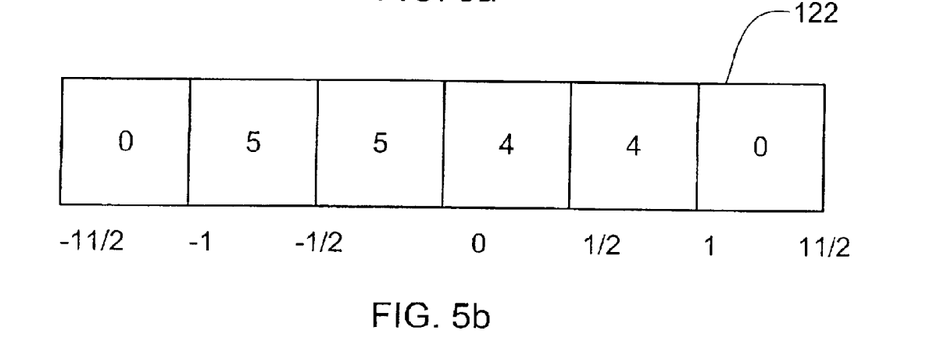
Figure 5C:
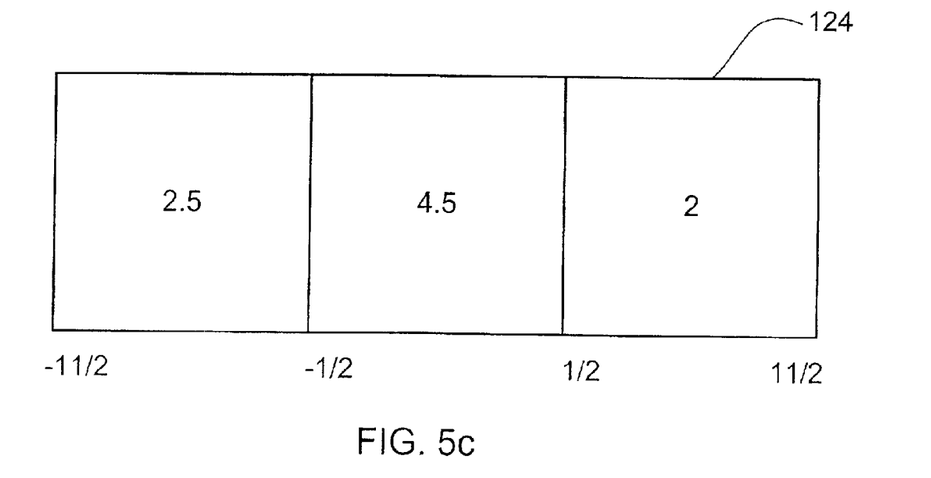
FIG. 5c is a row of a target intensity map created from the intermediate map row of FIG. 5b.

FIGS. 5a, 5b, and 5c show rows of a source map 120, intermediate map 122 and target map 124, respectively. The cells of the source map 120 have radiation intensity values of 5 and 4 and have edges located on gridlines at −1, 0, and 1. This geometry is incompatible with the geometry of a multi-leaf collimator that is to be used to deliver a radiation treatment. The target map 124 has the desired intensity map geometry, which has cell edges located along gridlines at −1½, −½, ½, and 1½. The intermediate map 122 is used to determine the radiation intensity values for the target intensity map 124. The intermediate map 122 is created using sampling points that are common to both the source map 120 and the target map 124. The intermediate map 122 therefore has cells positioned such that their edges are located at −1½, −1, −½, 0, ½, 1, and 1½. This intermediate intensity map 122 contains the sampling points of both the source intensity map 120 and the target intensity map 124. The values for the intermediate and target intensity maps 122, 124 are determined by interpolating or extrapolating the values of the cells of the source map 120 and intermediate map 122, respectively. The following shows the intensity values for the intermediate intensity map 122 which are obtained directly from the source map 120:

−1½→−1=0

−1→−½=5

$-½→0=5$ $0→½=4$ $½→1=4$ $1→1½=0$

The values for the cells of the target map 124 are calculated by taking the average of adjacent cells located within corresponding gridlines:

$-1½→-½=(0+5)/2=2½$ $-½→½=(5+4)/2=4½$ $½→1½=(4+0)/2=2$

The above process is performed for all rows and columns of an intensity map using interpolation and extrapolation in two dimensions, as is well known by those skilled in the art.

It should be noted that the sampling points do not have to be uniformly spaced in order to use the above described method. Typically, although not always, the input intensity map has uniformly spaced points, but the target map may not have uniformly spaced sampling points. The resolution in the x direction may be different than the resolution in the y direction, for example. Also, the spacing between samples in any direction may not be the same from one sample point to the next. For example, there may be some limitations as to the pencil beam sizes on the target map, in which case the spacing at those locations may be different. In this case, the intermediate map contains all of these irregular sampling points and may end up having irregularly spaced sampling points. The extrapolation and interpolation process is still performed as previously described. Alternatively, the irregularly spaced samples may be made regular in the intermediate map by increasing the resolution of the map.

Figure 6:
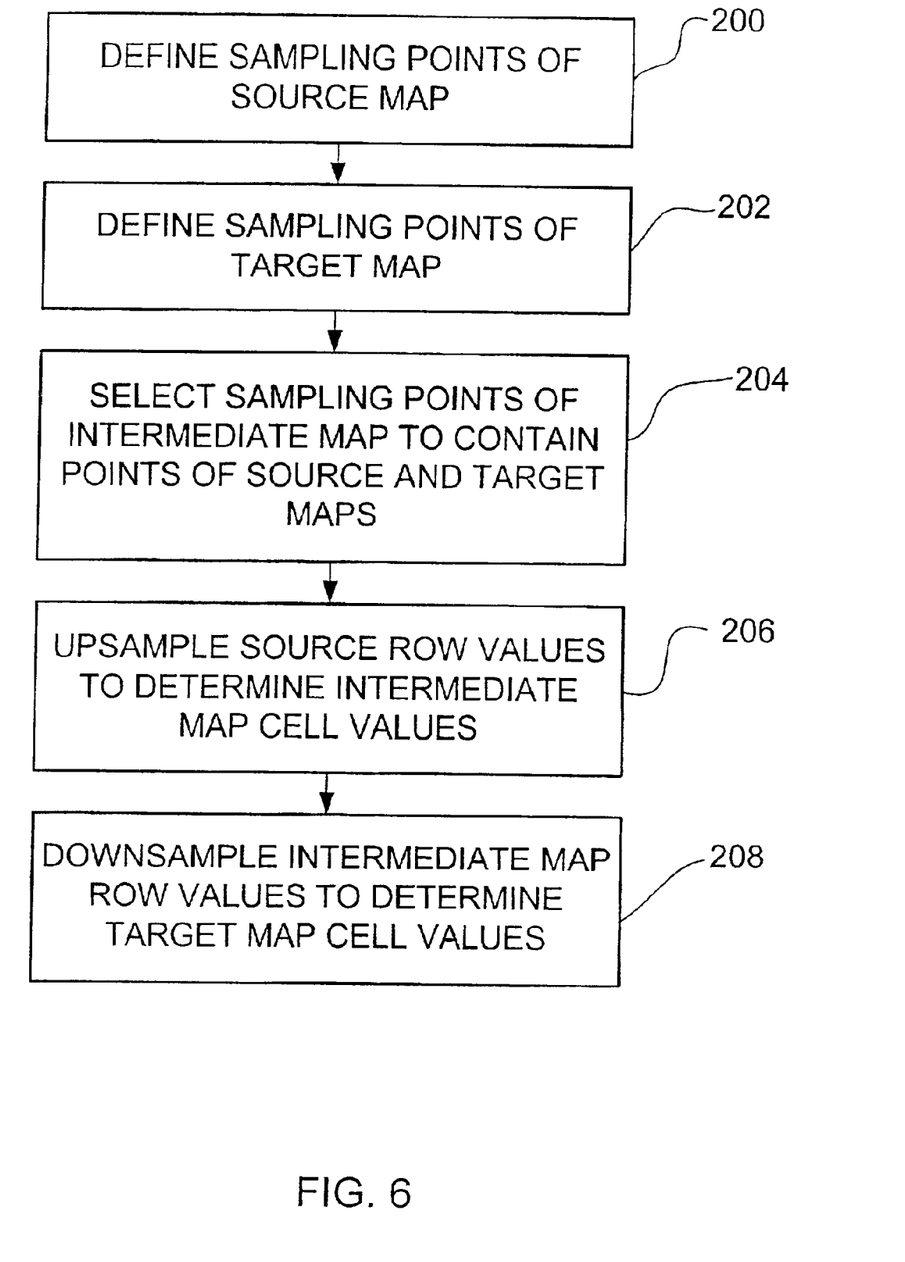
FIG. 6 is a flowchart illustrating a process of the present invention for converting an intensity map into a map that is compatible with a desired multi-leaf collimator geometry.

FIG. 6 is a flowchart illustrating a process of the present invention for converting a source intensity map into a target intensity map having a geometry compatible with a desired multi-leaf collimator configuration. Once the source map and target map geometries are received, sample points of the source map and the target map are defined (steps 200 and 202). The intermediate map geometry is defined to contain the sampling points of both the source map and the target map (step 204). The source values are upsampled to determine intermediate map cell values at step 206. The cell intensity values of the intermediate map are then downsampled to determine the target map cell values at step 208.

It will be observed from the foregoing that the method and system of the present invention have numerous advantages. For example, the method and system allow an intensity map to be delivered by a sequence of multi-leaf collimator shapes. Thus, treatment planning systems that produce incompatible map geometries can still be used to create intensity maps. Furthermore, a treatment planning system does not have to be reconfigured to provide an intensity map for a multi-leaf collimator having a different geometry. Errors in representing a two dimensional function are generally avoided since resampling is used rather than deletion and shifting of cells.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for converting a source intensity map into a target intensity map having a geometry compatible with a desired multi-leaf collimator configuration, each of the source intensity map and the target intensity map having a geometry defining sampling points of cells within the maps, the source intensity map having a geometry that is incompatible with the desired multi-leaf collimator configuration, the method comprising:

defining a field on an object for radiation delivery, said field including a plurality of cells defining the source intensity map, each of said plurality of cells having a treatment intensity level;

creating an intermediate intensity map geometry such that the intermediate map contains sampling points of the source intensity map and the target intensity map;

defining treatment intensity levels for cells of the intermediate map; and calculating treatment intensity levels for cells of the target intensity map based on the intensity level of the intermediate map cells.

2. The method of claim 1 wherein defining treatment intensity levels for the intermediate map cells comprises retrieving the treatment intensity levels from a treatment planning system and wherein the source intensity map and the intermediate intensity map have the same geometry and intensity levels.

3. The method of claim 1 wherein defining treatment intensity levels for the intermediate map cells comprises calculating the intermediate map treatment intensity levels based on the source map treatment intensity levels.

4. The method of claim 3 wherein calculating the intermediate map treatment intensity levels comprises interpolating or extrapolating using source map treatment intensity levels.

5. The method of claim 1 wherein calculating treatment intensity levels for cells of the target intensity map comprises down sampling values from the intermediate intensity map.

6. The method of claim 5 wherein down sampling values comprises performing an interpolation or extrapolation process.

7. The method of claim 1 further comprising delivering a radiation treatment with the desired multi-leaf collimator configuration from the target intensity map.

8. The method of claim 1 further comprising creating an intensity map for virtual micro intensity modulation radiation therapy based on the target intensity map.

9. A system for converting a source intensity map into a target intensity map having a geometry compatible with a desired multi-leaf collimator configuration, each of the source intensity map and the target intensity map having a geometry defining sampling points of cells within the map, the source intensity map having a geometry that is incompatible with the desired multi-leaf collimator configuration, the system comprising:

a processor operable to receive a source intensity map geometry, target intensity map geometry, and treatment intensity levels for cells of the source intensity map, create an intermediate map geometry containing sampling points of the source map and the target map, define treatment intensity levels for cells of the intermediate intensity map, calculate treatment intensity levels for cells of the target intensity map based on the intensity level of the intermediate map cells, and output the target intensity map; and memory configured to at least temporarily store the source intensity map, intermediate intensity map, and the target intensity map.

10. The system of claim 9 wherein receiving the treatment intensity levels and the geometry for the source map comprises receiving an intensity map from a treatment planning system and wherein the source map and the intermediate map have the same geometry and intensity treatment levels.

11. The system of claim 9 wherein the intermediate map treatment intensity levels are calculated from the source map treatment intensity levels.

12. The system of claim 9 further comprising a collimator having multiple leaves for blocking radiation from said source and defining an opening between the radiation source and said object, the collimator having the desired multi-leaf collimator configuration.

13. The system of claim 12 wherein the multi-leaf collimator is operable to provide radiation treatment with a resolution approximately one half of the width of the leaves.

\* \* \* \* \*